United States Patent [19]

Pokora et al.

[11] Patent Number: 5,178,762
[45] Date of Patent: Jan. 12, 1993

[54] SOYBEAN PEROXIDASE TREATMENT OF CONTAMINATED SUBSTANCES

[75] Inventors: Alexander R. Pokora, Pickerington; Mark A. Johnson, Chillicothe, both of Ohio

[73] Assignee: The Mead Corporation, Dayton, Ohio

[21] Appl. No.: 876,509

[22] Filed: Apr. 29, 1992

Related U.S. Application Data

[63] Continuation-in-part of Ser. No. 760,999, Sep. 17, 1991, abandoned, which is a continuation-in-part of Ser. No. 599,584, Oct. 18, 1990, Pat. No. 5,147,793.

[51] Int. Cl.$^5$ .......................... C02F 1/72; C02F 1/62; C02F 3/32
[52] U.S. Cl. .................... 210/632; 210/721; 210/759; 210/763; 210/912; 210/908; 210/909; 210/917; 210/928; 162/29; 162/190; 162/72
[58] Field of Search ........ 210/721, 728, 759, 912-914, 210/928, 908, 909, 917, 903, 632; 435/192, 262, 264, 41, 28; 162/29, 72 B, 190

[56] References Cited

U.S. PATENT DOCUMENTS

| | | | |
|---|---|---|---|
| 3,694,209 | 9/1972 | Matejec et al. | 96/48 |
| 4,370,199 | 1/1983 | Orndorff | 210/764 |
| 4,478,683 | 10/1984 | Orndorff | 210/764 |
| 4,485,016 | 11/1984 | Hopkins | 210/759 |
| 4,623,465 | 11/1986 | Klibanov | 210/759 |
| 4,778,753 | 10/1988 | Yamanishi et al. | 435/10 |
| 4,891,320 | 1/1990 | Aust et al. | 210/909 |
| 5,051,184 | 9/1991 | Taylor | 210/632 |
| 5,112,752 | 5/1992 | Johnson | 435/192 |

OTHER PUBLICATIONS

Alberti, B. N. and Klibanov, A. M., Laboratory of Applied Biochemistry, Enzymatic Removal of Dissolved Aromatics from Industrial Aqueous Effluents, No. 11, pp. 373-379 (1981).

Klibanov, A. M., Alberti, B. N., Morris E. D. and Felshin L. M., Laboratory of Applied Biochemistry, Enzymatic Removal of Toxic Phenols and Anilines from Waste Waters, pp. 414-421 (1980).

Booth, H.; Sanders, B. C. "Studies in Peroxidase Action Part X, The Oxidation of Phenols" *Journal of the Chemical Society*, Part I (1956) pp. 940-948.

Shannor, M. J. R.; Bartha, R. "Immobilization of Leachable Toxic Soil Pollutants by Using Oxidative Enzymes," *Applied and Environmental Microbiology*, 1988 54(7) pp. 1719-1723.

Gillikin J. W.; Graham, J. S.; "Purification and Development Analysis of the Major Anionic Peroxidase from the Seed Coat of Clycine Max," Plant Physiology, (1991) 96-214-220.

Roy-Arcand, L.; and Archibald, F. S. "Direct Dechlorination of Chlorophenolic Compounds by Laccases from Trametes (Coriolus) Versicolor," *Enzyme Microb. Technol.*, 1991, vol. 13, Mar, pp. 194-203.

Atlow S. C.; Bonadonna-Aparo L; Klibanov A. M.; "Dephenolization of Industrial Wastewaters Catalyzed by Polyphenol Oxidase," Biotechnology & Bioengineering, vol. XXVI, pp. 599-603 (1984).

*Primary Examiner*—Wilbur Bascomb, Jr.
*Assistant Examiner*—Neil M. McCarthy
*Attorney, Agent, or Firm*—Thompson, Hine and Flory

[57] ABSTRACT

A method for oxidizing organic and/or heavy metal contaminants in wastewaters, sludges, or soils containing such contaminants by contacting the wastewaters, sludges, or soils with soybean peroxidase and a peroxide.

18 Claims, No Drawings

SOYBEAN PEROXIDASE TREATMENT OF CONTAMINATED SUBSTANCES

This application is a continuation-in-part of U.S. application Ser. No. 07/760,999, abandoned filed Sep. 17, 1991, which is a continuation-in-part of U.S. application Ser. No. 07/599,584 filed Oct. 18, 1990 now U.S. Pat. No. 5,147,793.

BACKGROUND OF THE INVENTION

The present invention relates to a method for the treatment of contaminated substances such as wastewaters and soils to remove organic contaminates and/or heavy metals using soybean peroxidase (SBP), and a peroxide.

Existing methods for the removal of organic and inorganic pollutants from contaminated sources include adsorption, extraction, microbial and chemical oxidation, electrochemical techniques and irradiation. However, all of these methods suffer from serious shortcomings such as high costs, incompleteness of purification, formation of hazardous byproducts and low efficiency. see, e.g., M. W. Slein et al, *Degradation of Chemical Carcinogens*, Van Nostrand Reinhold Co., 1980; *Cleaning our Environment—A Chemical Perspective*, American Chemical Society, 1978. Therefore, alternative methods of removing aromatic compounds from wastewater are highly desirable.

The use of peroxidase enzymes to remove hazardous aromatic materials from wastewaters is well known. For example, Alberti and Klibanov, "Peroxidase for removal of Hazardous Aromatics form Industrial Wastewaters," *Biological Detoxication*, Chapter 22, 349-356 (1982) disclose that phenols and aromatic amines can be removed from wastewaters as high molecular weight polymers by the action of horseradish peroxidase enzymes on such aromatic compounds. The disclosed method relies on the ability to catalyze, with hydrogen peroxide, the oxidation of a variety of phenols and aromatic amines. Phenolic and aromatic amine-free radicals are generated and these free radicals diffuse from the active center of the enzyme into solution where they polymerize to form high molecular weight polyaromatic products which are insoluble and can be readily separated from the water by, e.g., filtration.

U.S. Pat. No. 4,623,465 to Klibanov discloses a method for removing aromatic substances such as phenols and aromatic amines from aqueous solutions by adding chemicals such as horseradish peroxidase enzyme and peroxide substrates to such solutions which contain two or more different aromatic substances. According to Klibanov '465, phenols are removed from water with about 75% efficiency by horseradish peroxidase and peroxide at a pH of 5.5 at room temperature. However, when another aromatic compound such as orthodianisidine, benzidine or 8-hydroxyquinoline is added to the phenol, then the phenol and the other aromatic substance are both removed form the solution with better than 99.5% efficiency.

U.S. Pat. No. 4,478,683 to Orndorff describes a method for enzymatically killing and controlling the growth of microorganisms in industrial wastewater streams by the catalytic oxidation of monophenolic compounds added to or naturally occurring in the stream. The preferred enzyme is a plant peroxidase, e.g., from horseradish, turnip, etc.

Shannon et al., "immobilization of Leachable Toxic Soil Pollutants", *Appl. Env. Microbiol.*, 54, No. 7, 1719-1723, (1988) discuss the use of horseradish peroxidase to immobilize phenolic pollutants in sand and soil columns. The immobilized pollutants were non-leachable from the sand and soil for extended periods of time.

Because of the wide use of chlorine as a bleaching agent for chemically produced wood pulps in the pulp and paper industry, dilute pulp mill bleaching effluents contain undesirable levels of adsorbable organic halogens (AOX) in the form of chlorophenols, chloroaliphatics, chlorocatechols, polymerized chloroaromatics, etc. Also, chlorophenols are major intermediates of phenoxyalkanoate herbicides and other pesticides which retain their toxic properties for an indefinite period of time since they easily form soil-bound residues. The effect of chlorinated compounds such as pentachlorinatedphenol (PCP), polychlorinated biphenyls (PCB), chlorinated benzene, etc. released into the environment is an immediate concern of the entire population, and increasingly stringent government standards are requiring that the total levels of such chlorinated compounds released into the environment be substantially reduced.

Roy-Arcand and Archibald, "Direct Dechlorination of Chlorophenolic Compounds by Laccases form Trametes (Coriolus) Versicolor", *Enzyme Microb. Technol.*, Vol. 13, pp. 194-203 (1991) disclose that horseradish peroxidase will dechlorinate chlorinated compounds present in pulp mill bleach plant effluents. The authors suggest that the enzymatic treatment of such wastewaters using horseradish peroxidase offers a potentially superior method of wastewater treatment.

Ferrer et al. "Decolorization of Kraft Effluent by Free and Immobilized Lignin Peroxidase and Horseradish Peroxidase", *Biotechnology Letters*, Vol. 13, No. 3, 577, 582 (1991) disclose that in the free state some enzymes such as lignin peroxidase and horseradish peroxidase will remove color from kraft effluents but in all cases studied, the immobilized enzymes were considerably more efficient than the enzyme in the free form.

Wigfield et al, "Kinetics and Mechanisms of Oxidation of Mercury by Peroxidase", *Can. J. Chem.*, Vol. 63, 2940-2944, (1985) reported the kinetics of the oxidation of zero-valent mercury by horseradish peroxidase.

However, in the past, peroxidase enzymes have not been available at a cost and in a purity amenable to many biocatalytic processes such as for the treatment of contaminated waters, and particularly wastewater treatment. For example, horseradish roots, a common source of horseradish peroxidase (HRP), are cultivated generally in small quantities and are propagated through root cuttings, thus making it difficult to scale up production. The limited availability of the horseradish root extract coupled with the shortage of alternative sources of enzyme has created a very expensive market for such enzymes. Accordingly, there exists in the marketplace a need for an abundant and relatively inexpensive source of peroxidase for use in treating contaminated waters, and particularly for use in wastewater treatment to remove hazardous or toxic materials.

SUMMARY OF THE INVENTION

It has been found that soybean peroxidase has better temperature and solvent stability and a higher redox potential than horseradish peroxidase and that it is much more economical for use in bioremediation processes because it can be readily obtained from soybean hulls which are very plentiful and inexpensive.

A principal object of the present invention is to improve the biocatalytic oxidative process for removing contaminants from waters, soils and sludges through the use of peroxidases from soybeans or for converting these contaminants to less toxic or more easily removable forms. The invention is particularly useful in remediating the effects of adsorbable organic halides (AOX), phenols, aromatic amines, color bodies, heavy metals, and/or mixtures thereof.

The present invention is particularly useful for the biocatalytic removal or conversion of such undesirable materials from industrial wastewaters, soils and sludges and for the conversion of hazardous pollutants to innocuous or inert materials in soils where removal of such materials is difficult or impossible.

Accordingly, one embodiment of the present invention is a method for treating contaminated substances such as waters, soils and sludges which comprises contacting the contaminated substances with a peroxide substrate in the presence of soybean peroxidase.

One embodiment of the present invention is a method for enzymatic treatment of wastewaters containing adsorbable organic halides (AOX), phenols, aromatic amines, color bodies, heavy metals, or mixtures thereof which comprises reacting the contaminants in the wastewaters with soybean peroxidase and, in some cases with soybean seed hulls as a source of soybean peroxidase, and hydrogen peroxide to remove the contaminants or convert them to a less hazardous or more easily removable form. The action of the peroxidase is basically one of free radical generation and oxidation. AOX compounds are believed to be dehalogenated with the production of non-toxic halides. Phenols and amines are polymerized; the polymer may be removed from wastewaters by filtration or sedimentation and is less harmful in the soil than the unpolymerized phenol and amine. Heavy metals are oxidized to ionic forms which can be removed by ion exchange, chelation or other processes. Color bodies are degraded or precipitated and removed from waste streams by filtration, sedimentation or other method of separation.

This invention is not limited to the removal of the aforementioned contaminants but can also be used to remove other aromatic and other organic compounds. For example, certain compounds such as naphthalene do not react directly with peroxidase and peroxide to create free radicals. However, if free radicals are created by the action of peroxidase on other substrates, those free radicals may be capable of reacting with naphthalene and such other compounds, binding them within the polymerized precipitate and thereby removing them from an aqueous solution. Any contaminant may be remediated by this invention to the extent that it is capable of participating in a biocatalytic oxidative reaction involving free radicals. Such contaminants may be directly affected by enzymes, or by free radicals on other substances.

Other objects and advantages will be apparent from the following description and the appended claims.

DEFINITIONS

A "unit" of peroxidase means the amount of peroxidase which produces a change of 12 absorbance units measured at 1 cm pathlength in one minute at 420 nm when added to a solution containing 100 mM potassium phosphate, 44 mM pyrogallol and 8 mM hydrogen peroxide and having a pH of 6 (Sigma Chemical Co. Peroxidase Bulletin).

The term "color bodies" means materials which color wastewaters such as lignin fragments and lignin derivatives having a molecular weight up to 15,000.

The term "wastewaters" is used herein to mean polluted natural waters, industrial wastewaters, and any waters which are treated as part of a water treatment program. The term does not read on solutions prepared as starting materials for the commercial synthesis or manufacture of phenolic resins.

The term "soils" is used herein to describe soils and particularly humus soils which contain contaminants such as adsorbable organic halogens (AOX), phenols, heavy metals, aromatic amines or mixtures thereof.

The term "sludges" is used herein to describe the particulate matter removed from contaminated waters.

DETAILED DESCRIPTION OF THE INVENTION

In accordance with the present invention, the contaminated substance is remediated by reacting the contaminant with a peroxide in the presence of the peroxidase under conditions sufficient to convert the contaminants to insoluble and/or non-hazardous materials. In the case of soils, a solution of the peroxidase or the crushed soybean seed hulls is physically mixed with the soil using a tiller or other mixing means and a dilute solution of the peroxide is sprayed or otherwise contacted with the soil-peroxidase mixture and allowed to react whereby the contaminants are converted to insoluble and/or non-hazardous materials. It is not necessary to remove such materials from the soil.

Sludges which are generally slurries can be slurried with the peroxidase and peroxide to convert the contaminants to insoluble, non-hazardous, or more readily removed materials.

With respect to the purification of contaminated waters, the contaminants are either converted to nonhazardous materials or they may be removed as an insoluble product by reacting the contaminated waters with a soybean peroxidase enzyme and a peroxide. Preferably, the waters and soybean peroxidase are pre-mixed or slurried (in the case of hulls) and the peroxide is added incrementally or gradually over a period of time. Excess peroxide tends to inhibit the reaction. The enzyme may be provided as a solution in water, on a solid support or the soybean seed hulls in the ground form may be used directly. For example; the contaminated water and the ground soybean seed hulls may be slurried together and the peroxide added at a controlled rate. Alternatively, ground soybean seed hulls can be packed in a column and the peroxide and the contaminated water passed over the packed hulls. It is not clear whether the soybean peroxidase enzyme is being extracted by the water during the reaction or whether the peroxidase reacts similar to an immobilized enzyme. A combination of both mechanisms may occur.

The amount of soybean peroxidase enzyme needed will depend on its activity. The enzyme is not consumed in the reaction but, in general, it does gradually lose activity during the course of the reaction. Typically, the amount of enzyme to be reacted will be about 0.05 to 5 units and more typically 0.5 to 1 units per liter of the contaminated waters.

In those instances when the soybean seed hulls are used directly in the reaction to provide the enzyme, the hulls will be used in an amount sufficient to provide the required amount of enzyme as indicated above. It is estimated that about 1 to 10 grams of hulls per liter of contaminated water will suffice. The exact amount will depend somewhat on the activity of the hulls. Older hulls are less active than fresher hulls.

The peroxide used is typically hydrogen peroxide, but other peroxides are also useful. Examples of other potentially useful peroxides include methyl peroxide, ethyl peroxide, etc. The peroxide is reacted in an amount of about 0.1 to 10 mmoles per liter of contaminated waters and more typically about 0.5 to 2 mmoles per liter of waters. The preferred oxidizing agent, hydrogen peroxide, may be dissolved in water for addition to the contaminated water. Its concentration may range from about 5 to 20 M. In adding the peroxide, it is necessary to limit the addition because excess peroxide will inhibit the reaction. It is generally desirable to use a ramped addition in which higher amounts of peroxide are used at the beginning of the reaction when the peroxide is consumed rapidly and scaled down amounts of peroxide are used in the later stages.

For reaction on soils and sludges, higher applications of peroxidase and peroxide may be required.

Reaction temperature may vary with the contaminant. Soybean peroxidase has unusual thermal stability even at temperatures of 60° C. or higher (up to 90° without water) for 30 minutes or more. In most cases, the wastewaters will be treated at their ambient temperature to reduce cost although more efficient removal might be obtained if the waters were heated to about 30° C. Soils and sludges may be treated at higher temperatures.

The activity of peroxidases is pH dependent. Another of the advantages of soybean peroxidase is that it retains its activity over a broad pH range. It is active throughout the pH range of 3 to 13. The oxidative reactions are typically carried out at a pH in the range of 3 to 10 and, particularly, 4 to 9. A pH may be selected at which the enzyme is highly active, but for economic and environmental reasons, the pH of the water will typically be maintained at about 7. This will vary with the nature of the enzyme and its source. Buffers can be used to maintain pH, but are not usually required. One example of a useful buffer is a potassium phosphate buffer. Soils and sludges can be modified to bring their pH into the aforementioned ranges, but because of the broad activity of soybean peroxidase it will be possible to treat the soil or sludge "as is" in most cases.

Peroxidases, being water soluble, are easily harvested by homogenizing the protein source (e.g., the whole bean or the hulls) with water, filtering the homogenate, and retaining the filtrate. In a particularly preferred process, the hulls are homogenized in water, the homogenate is heated to 30° to 70° C. and/or the pH is adjusted to alkaline, and the homogenate is centrifuged. Further purification may be accomplished by ultrafiltration.

Although the peroxidase need not be purified for the purpose of this invention, further purification can also be readily accomplished by treating the enzyme to remove proteinaceous and lipophilic impurities by adding to a solution of the enzyme a protein fixative or a detergent and forcing the enzyme to precipitate as described in copending U.S. application Ser. No. 07/599,584 now U.S. Pat. No. 5,147,793.

Soybean seed hulls in ground form are conveniently supplied form commercial soybean processors and may be used directly as such without any further preparation.

The action of the peroxidase in accordance with the invention varies with the contaminant. In some cases, the reaction of the contaminant generates a product which can be removed whereas in other cases the contaminant may react to form a product which is less harmful than the contaminant itself. Phenols and aromatic amines polymerize in the presence of soybean peroxidase and hydrogen peroxide. This reaction is described in the literature for horseradish peroxidase. The reaction of soybean peroxidase is described in allowed U.S. application Ser. No. 599,584 filed Oct. 18, 1990 now U.S. Pat. No. 5,147,793. The polymerization product can be readily removed from wastewater by sedimentation. The polymerized product is not toxic or substantially less toxic than the unpolymerized monomer and may remain in soils and sludges treated in accordance with the invention.

Heavy metals are oxidized to higher valencies in accordance with the invention. Examples of heavy metals which can be removed in accordance with the invention include Hg, Ag, Tl, Sb, Te, Pb, As, Se or Bi. These metals are oxidized in the presence of peroxidase and peroxide to ions which can be more easily separated using well known techniques such as ion exchange and chelation.

One of the most typical examples of colored bodies removable in accordance with the invention is lignin fragments. Lignin reacts similar to phenol in the present invention thereby enabling the separation of colored bodies from waste streams by precipitation or sedimentation.

Those skilled in the art will appreciate that the present invention is not limited to the foregoing contaminants. The effects of substantially any contaminant which is capable of reacting with the peroxidase in the presence of peroxide may be remediated to some useful degree, in accordance with the present invention. In particular, any contaminant which can be oxidized by a peroxide in the presence of soybean peroxidase may be treated in accordance with the invention.

The invention is illustrated in more detail by the following non-limited example.

EXAMPLE 1

0.8 grams of 3,5-dimethoxyphenol was dissolved in 8 ml acetone and the solution was added to 8 l of tap water. The phenol solution was divided into seven one-liter beakers and stirred with a magnetic stirrer at room temperature. Varying amounts of hammermill-ground, dry soybean seed hulls were added to each beaker followed by the addition of 0.1 ml of 30% hydrogen peroxide to each beaker. The solution was stirred for 30 minutes and another aliquot (0.1 ml) of 30% hydrogen peroxide was added.

Samples were taken from each beaker before the first peroxide addition, after 30 minutes of stirring with the first peroxide addition, and after 60 minutes of stirring (total) with both peroxide additions. Each sample was filtered using a 0.2 $\mu$m polytetrafluoroethylene (PTFE) membrane filter and analyzed for 3,5-dimethoxyphenol using high pressure liquid chromatography (HPLC).

A standard curve of the known response to 3,5-dimethoxyphenol was used to quantify the compound. Each sample was also assayed for peroxidase activity by the Pyrogallol procedure (Sigma Chemical Co., Peroxidase (Horseradish) Bulletin). The results are shown in Table I.

TABLE 1

| Sample | g. Hulls per Liter | Peroxidase Units/ml | 3,5-Dimethoxy phenol content, | | | |
|---|---|---|---|---|---|---|
| | | | mg/ml Zero Time | After 30 min. | After 60 min. | % Decline |
| 1 | None | 0 | 0.013 | 0.013 | 0.013 | 0 |
| 2 | 0.16 | 0.005 | 0.104 | 0.105 | 0.103 | 0 |
| 3 | 0.33 | 0.001 | 0.105 | 0.102 | 0.097 | 7.6 |
| 4 | 1.06 | 0.0596 | 0.104 | 0.080 | 0.072 | 31.0 |
| 5 | 2.16 | 0.078 | 0.104 | 0.057 | 0.041 | 61.0 |
| 6 | 4.14 | 0.185 | 0.103 | 0.039 | 0.014 | 86.0 |
| 7 | 8.47 | 0.525 | 0.102 | 0.030 | 0.007 | 93.0 |

The results show that each sample has the same expected phenol content 0.8 g/8 l=0.1 mg/ml and that with increasing addition of hulls, no phenol is removed from solution by absorption to the hulls. Rather, the mechanism of removal of phenol from solutions as supported by the results is the action of peroxidase on the phenol. With increasing addition of hulls, the peroxidase activity increases and the phenol is removed from solution with increasing efficiency. Peroxidase catalyzed polymerization of the phenolic compound leads to an insoluble polymer, an innocuous and environmentally less toxic form of the phenol.

The cost of this treatment is projected to be significantly less than using horseradish peroxidase or other similarly priced enzymes (Coprinus peroxidase, ligninase, etc.) The lowest commercial price for horseradish peroxidase has been $110.00 per million pyrogallol units (from Finnsugar Biochemical) as an Industrial Grade (IG) enzyme. Treatment of 1,000 gallons of wastewaters to achieve 93% removal of phenolic compounds at a starting level of 0.1 g per liter (shown in the data) would cost $218.00 for the same amount in units of IG horseradish peroxidase. At a commodity price of $55.00 per ton quoted for ground soybean hulls from Cargill, the cost of this treatment of 1,000 gallons would be $1.94 for soybean peroxidase, or 112 times lower than horseradish peroxidase.

The redox potential sof HRP and SBP were measured with respect to the substrates shown in Table 2.

TABLE 2

| REDOX POTENTIAL COMPARISON BETWEEN SBP AND HRP | | | |
|---|---|---|---|
| Substrate | E1/2(V) | HRP* | SBP* |
| pentamethoxybenzene | 1.07 | 2.50 | 8.76 |
| 1,2,3,5-tetramethoxybenzene | 1.09 | 0.30 | 3.02 |
| 1,2,4 trimethoxybenzene | 1.12 | 1.64 | 9.23 |
| hexamethoxybenzene | 1.24 | 0 | 0.22 |
| 1,4-dimethoxybenzene | 1.34 | 0 | 0.072** |

*All values in ΔAbsorption/(mg enzyme-min)
**Curve of ΔAbsorption/time slopes upward as reaction proceeds Having described the invention in detail and by reference to preferred embodiments thereof, it will be apparent that modifications and variations are possible without departing from the scope of the invention defined in the appended claims.

What is claimed is:

1. A method for oxidizing organic and/or heavy metal contaminants in wastewaters, sludges, or soils containing said contaminants which comprises contacting said wastewaters, sludges or soils with soybean peroxidase and a peroxide.

2. The method of claim 1 wherein said wastewaters, sludges or soils are contacted with ground soybean hulls.

3. The method of claim 1 wherein said peroxide is hydrogen peroxide.

4. The method of claim 3 wherein said method is for treating wastewater.

5. The method of claim 4 wherein said wastewater is contacted with about 0.05 to 5 units of soybean peroxidase per liter of wastewater.

6. The method of claim 5 wherein said wastewaters are treated with about 0.1 to 10 mmoles hydrogen peroxide per liter of said wastewaters, said treatment conducted at a temperature up to about 60° C. and at a pH of about 3 to 10.

7. The method of claim 6 wherein said treatment reduces the amount of AOX in said wastewater.

8. The method of claim 6 wherein said treatment reduces the amount of phenols and aromatic amines in said wastewater.

9. The method of claim 6 wherein said treatment reduces the amount of color bodies, heavy metals, or mixtures thereof.

10. The method of claim 9 wherein said wastewater is pulp mill effluents.

11. The method of claim 6 wherein said treatment oxidizes heavy metals and renders them more readily removable.

12. The method of claim 3 wherein said method is for treating soils or sludges.

13. The method of claim 12 wherein said soils or sludges are mixed with soybean peroxidase and a solution of hydrogen peroxide.

14. The method of claim 13 wherein said soybean peroxidase is mixed as ground soybean hulls.

15. The method of claim 13 wherein said method converts phenols or aromatic amines to less hazardous polymeric phenols or amines.

16. The method of claim 11 wherein said treatment includes the additional step of removing said heavy metals.

17. The method of claim 16 wherein said heavy metals are removed by ion exchange or chelation.

18. The method of claim 6 wherein said hydrogen peroxide is added under conditions such that said peroxide does not substantially inhibit the reaction of said peroxidase.

* * * * *